United States Patent [19]

Gyllang et al.

[11] Patent Number: 4,649,051

[45] Date of Patent: Mar. 10, 1987

[54] BEVERAGE PRODUCT

[75] Inventors: Hans E. Gyllang, Skogsvägen; Bjorn T. Ekblom, Backshigan; Vera V. Wesshagen, Högbyvägen; Kjell Y. Ericson, Bragevägen, all of Sweden

[73] Assignee: AB Pripps Bryggerier, Bromma, Sweden

[21] Appl. No.: 692,054

[22] Filed: Jan. 16, 1985

[30] Foreign Application Priority Data

Nov. 23, 1984 [EP] European Pat. Off. ............ 84850363

[51] Int. Cl.$^4$ .................... A61K 33/06; A61K 33/10; A61K 33/08; A61K 31/70
[52] U.S. Cl. ................................. 424/154; 424/156; 424/157; 514/23
[58] Field of Search .................... 424/154, 156, 157; 514/23, 54

[56] References Cited

U.S. PATENT DOCUMENTS

| 4,312,856 | 1/1982 | Korduner et al. | 424/145 |
| 4,322,407 | 3/1982 | Ko | 424/128 |
| 4,448,770 | 5/1984 | Epting | 424/153 |

FOREIGN PATENT DOCUMENTS

0644737  8/1984  Liechtenstein ............ 424/152

Primary Examiner—Donald B. Moyer
Assistant Examiner—John W. Rollins, Jr.
Attorney, Agent, or Firm—Abelman Frayne Rezac & Schwab

[57] ABSTRACT

Beverage product, especially adapted for rapid administration of water and carbohydrates to the human body during periods of heavy muscle work, which consists of a preferably monosaccharide-free solution containing 3-25% by weight of a mixture of soluble oligosaccharides with DP values between 2 and 10 inclusive, the average DP value of the oligosaccharide mixture preferably being in the range 3-5; at least one physiologically acceptable alkalizing compound or compound combination; and optionally salts occuring in body liquids and suitably aroma and taste-improving substances, all of them in minor amounts; the solution's content of the physiologically acceptable alkalizing compound or compound combination being such that when the beverage is consumed during heavy muscle work (e.g. at 60% of the maximal aerobic capacity) in an amount of 250 mls each fifteenth minute during one hour gives an increase of the pH value in the vertricle contents to above 3.5, preferably above 4.5, especially above 7.0. A process for preparing the beverage product and a process for rapidly replacing water lost by perspiration and preventing a decrease of the glucose content of blood during periods of heavy muscle work.

11 Claims, 8 Drawing Figures

Fig.2

Solution acc. to Example 2 in US 4,312,856 1.5 litres/1.5 h

| Participants | Blood sugar level, mmoles/litre | | | | | | | | Pulse frequence | | | | | | | |
|---|---|---|---|---|---|---|---|---|---|---|---|---|---|---|---|---|
| | 0 | 15 | 30 | 45 | 60 | 75 | 90 | 0 | 15 | 30 | 45 | 60 | 75 | 90 | min. |
| A | 5.76 | 6.81 | 8.05 | 6.57 | 5.69 | 5.86 | 5.60 | 47 | 139 | 146 | 145 | 150 | 152 | 152 | |
| B | 4.45 | 5.04 | 5.73 | 6.52 | 7.02 | 5.78 | 5.14 | 46 | 150 | 152 | 152 | 150 | 155 | 156 | |
| C | 5.13 | 4.55 | 5.39 | 5.40 | 5.67 | 4.95 | 5.10 | 46 | 135 | 140 | 144 | 147 | 147 | 150 | |
| D | 4.53 | 5.65 | 6.64 | 5.60 | 4.92 | 5.14 | 4.23 | 42 | 122 | 130 | 128 | 128 | 128 | 130 | |
| E | 3.98 | 3.75 | 5.20 | 4.49 | 3.95 | 4.17 | 4.27 | 48 | 128 | 128 | 124 | 128 | 130 | 130 | |
| F | 3.39 | 4.52 | 5.70 | 4.84 | 4.94 | 4.32 | 4.59 | 48 | 107 | 108 | 110 | 112 | 111 | 111 | |
| G | 5.37 | 7.38 | 8.56 | 5.85 | 5.44 | 5.20 | 5.23 | 58 | 136 | 141 | 145 | 154 | 156 | 156 | |
| MV | 4.66 | 5.39 | 6.47 | 5.61 | 5.38 | 5.06 | 4.88 | 48 | 131 | 135 | 135 | 138 | 140 | 141 | |
| SD | 0.82 | 1.31 | 1.34 | 0.79 | 0.94 | 0.65 | 0.52 | 5 | 14 | 15 | 15 | 16 | 17 | 17 | |
| SC | 0.31 | 0.50 | 0.51 | 0.30 | 0.36 | 0.25 | 0.20 | 2 | 5 | 6 | 6 | 6 | 6 | 7 | |

Fig. 3

Solution II 1.5 litres/1.5 h

| Participants | Blood sugar level; mmoles/litre | | | | | | | | Pulse frequence min. | | | | | | |
|---|---|---|---|---|---|---|---|---|---|---|---|---|---|---|---|
| | 0 | 15 | 30 | 45 | 60 | 75 | 90 | 0 | 15 | 30 | 45 | 60 | 75 | 90 |
| A | 4.90 | 6.66 | 6.15 | 5.46 | 5.57 | 5.16 | 5.56 | 48 | 140 | 148 | 150 | 144 | 144 | 144 |
| B | 4.46 | 5.60 | 6.68 | 6.45 | 5.92 | 5.34 | 4.64 | 44 | 145 | 150 | 151 | 151 | 155 | 157 |
| C | 5.27 | 5.71 | 5.27 | 5.18 | 5.14 | 5.55 | 5.52 | 48 | 148 | 152 | 158 | 162 | 162 | 160 |
| D | 4.50 | 5.35 | 6.67 | 5.42 | 5.30 | 4.96 | 5.69 | 44 | 124 | 132 | 132 | 132 | 134 | 132 |
| E | 4.70 | 4.34 | 5.35 | 5.15 | 4.90 | 4.56 | 4.75 | 45 | 130 | 134 | 132 | 136 | 136 | 138 |
| F | 3.63 | 3.97 | 4.73 | 4.35 | 4.12 | 3.99 | 4.04 | 51 | 119 | 119 | 122 | 125 | 122 | 122 |
| G | 4.41 | 4.95 | 5.81 | 4.20 | 3.88 | 4.05 | 4.80 | 58 | 140 | 142 | 144 | 145 | 142 | 140 |
| MV | 4.55 | 5.23 | 5.81 | 5.17 | 4.98 | 4.80 | 5.00 | 48 | 135 | 140 | 141 | 142 | 142 | 142 |
| SD | 0.51 | 0.90 | 0.74 | 0.75 | 0.74 | 0.62 | 0.61 | 5 | 11 | 12 | 13 | 12 | 13 | 13 |
| SC | 0.19 | 0.34 | 0.28 | 0.28 | 0.28 | 0.23 | 0.23 | 2 | 4 | 5 | 5 | 5 | 5 | 5 |

Fig. 4

| Solution III 1.5 litres/1.5 h | | Blood sugar level; mmoles/litre | | | | | | | Pulse frequence | | | | | | | |
|---|---|---|---|---|---|---|---|---|---|---|---|---|---|---|---|---|
| Participants | 0 | 15 | 30 | 45 | 60 | 75 | 90 | 0 | 15 | 30 | 45 | 60 | 75 | 90 |
| A | 4.72 | 5.80 | 5.60 | 4.60 | 4.81 | 4.78 | 4.63 | 46 | 133 | 134 | 134 | 138 | 138 | 138 |
| B | 3.93 | 5.62 | 7.48 | 8.44 | 8.57 | 6.92 | 5.52 | 40 | 138 | 148 | 146 | 150 | 148 | 150 |
| C | 4.55 | 5.02 | 6.24 | 4.80 | 4.98 | 4.80 | 5.00 | 48 | 135 | 138 | 142 | 140 | 145 | 142 |
| D | 4.74 | 5.71 | 6.78 | 5.46 | 5.22 | 5.14 | 5.16 | 48 | 130 | 136 | 139 | 142 | 140 | 142 |
| E | 3.62 | 4.40 | 5.05 | 4.17 | 4.55 | 4.11 | 4.10 | 44 | 130 | 130 | 126 | 130 | 126 | 125 |
| F | 4.21 | 4.26 | 5.69 | 4.59 | 4.65 | 4.51 | 4.33 | 52 | 114 | 115 | 118 | 118 | 118 | 114 |
| G | 5.11 | 6.62 | 5.81 | 5.52 | 4.90 | 5.15 | 4.76 | 58 | 150 | 147 | 148 | 150 | 150 | 152 |
| MV | 4.41 | 5.35 | 6.09 | 5.37 | 5.38 | 5.06 | 4.79 | 48 | 133 | 135 | 136 | 138 | 138 | 138 |
| SD | 0.52 | 0.84 | 0.82 | 1.44 | 1.42 | 0.90 | 0.49 | 6 | 11 | 11 | 11 | 11 | 12 | 14 |
| SC | 0.20 | 0.32 | 0.31 | 0.54 | 0.54 | 0.34 | 0.18 | 2 | 4 | 4 | 4 | 4 | 4 | 5 |

Fig. 6

| Solution acc. to US 4,312,856 1.5 litres/1.5 h | | Weight change kgs. | Liquid volume to the body, mls. | Ventricle sample pH | Ventricle sample Sugar amount to the body, grams |
|---|---|---|---|---|---|
| Participants | A | −0.1 | 1,126 | 2.75 | 94.9 |
| | B | +0.4 | 850 | 2.98 | 83.4 |
| | C | −0.1 | 1,133 | 2.37 | 106.6 |
| | D | +0.1 | 1,355 | 1.38 | 113.8 |
| | E | +0.1 | 599 | 4.11 | 103.4 |
| | F | +0.4 | 1,312 | 2.28 | 120.0 |
| | G | +0.2 | 1,228 | 3.41 | 108.0 |
| | MV | +0.1 | 1,086 | 2.75 | 104.3 |
| | SD | | 271 | 0.87 | 12.1 |
| | SC | | 102 | 0.33 | 4.6 |

Fig.7

| Solution II 1.5 litres/1.5 h Participants | Weight change kgs. | Liquid volume to the body, mls. | Ventricle sample pH | Ventricle sample Sugar amount to the body, grams |
|---|---|---|---|---|
| A | ±0 | 1.338 | 5.42 | 119.0 |
| B | -0.1 | 1.296 | 6.66 | 106.3 |
| C | ±0 | 1.199 | 6.00 | 100.8 |
| D | ±0 | 865 | 1.94 | 80.3 |
| E | +0.1 | 1.267 | 1.92 | 106.2 |
| F | +0.2 | 1.465 | 2.79 | 118.3 |
| G | +0.2 | 1.356 | 7.69 | 110.8 |
| MV | +0.1 | 1.255 | 4.63 | 106.0 |
| SD |  | 191 | 2.38 | 13.1 |
| SC |  | 72 | 0.90 | 5.0 |

Fig. 8

| Solution III 1.5 litres/1.5 h Participants | Weight change kgs. | Liquid volume to the body, mls. | Ventricle sample pH | Ventricle sample Sugar amount to the body, grams |
|---|---|---|---|---|
| A | ±0 | 1.423 | 7.51 | 116.8 |
| B | +0.3 | 1.323 | 7.94 | 116.1 |
| C | −0.1 | 1.026 | 4.88 | 118.8 |
| D | +0.2 | 1.410 | 1.62 | 118.7 |
| E | +0.2 | 1.282 | 2.27 | 113.1 |
| F | +0.2 | 1.409 | 1.77 | 117.0 |
| G | +0.2 | 1.290 | 8.24 | 115.7 |
| MV | +0.1 | 1.309 | 4.89 | 116.6 |
| SD | | 138 | 3.02 | 1.9 |
| SC | | 52 | 1.14 | 0.7 |

BEVERAGE PRODUCT

The present invention relates to a beverage product which is especially suitable for rapid administration of water and carbohydrates to the human body during periods of heavy muscle work. The invention also comprises a process for preparing the said beverage product and a process for replacing water lost by perspiration and for preventing a decrease of the glucose content of the blood during periods of heavy muscle work.

During relatively extended periods of heavy muscle work the work capacity of an individual is delimited by several factors, such as a too low blood sugar concentration and loss of liquid by perspiration. The blood sugar content decreases during muscle work and the carbohydrate reserves in the liver and in the muscles are relatively small and are consumed after a short period of time due to the muscles' increased consumption thereof. The losses of liquid and also mineral salts can be considerable and they depend primarily on the intensity of the work and the ambient temperature.

It is known that administration of carbohydrate-containing aqueous solutions during work causes an increased blood sugar concentration, an increased insulin level and a readjustment of the metabolism of the liver in a glycogen-saving direction. After consumption of such solutions they will immediately enter into the ventricle. However, in the ventricle no absorption of water or carbohydrates occurs. Such absorption occurs only when the solution has passed through the pylorus into the duodenum. The ventricular emptying rate into the duodenum is an essential delimiting factor for maximal administration of water and carbohydrates during work. The pylorus is normally closed and its opening is essentially controlled by several factors. It is known that one such factor is the osmotic pressure of the ventricular contents. According to the present invention it has been found that one further such important factor is the pH value of the ventricular contents. By increasing the pH of the ventricular contents toward a neutral value (i.e. pH 7) or even an alkaline value (i.e. above 7) it has thus surprisingly been found that the passage of the ventricular contents through pylorus can be accelerated considerably.

One purpose of the invention is, as mentioned above, to achieve a beverage product which, dissolved in water, comprises blood sugar level-increasing carbohydrates in an amount adapted to different work and ambient conditions, suitably in combination with dissolved mineral salts of the type occurring in body liquids such as perspiration; this beverage product shall contain a physiologically acceptable alkalizing compound or compound combination which, after administration of the beverage product, increases the pH of the ventricular contents to such an extent that pylorus is brought to open so that the ventricular contents can pass therethrough for absorption in the duodenum.

From the U.S. Pat. No. 4,312,856 a beverage product is previously known which in a similar manner after consumption has a shortened residence time in the ventricle. The composition of this beverage product is such that it has as osmotic pressure which, in relation to the contents of carbohydrates and salts which are optionally present, has a so low osmotic pressure as possible which as pointed out above is of importance for the desired rapid passage through the pylorus. Also in the beverage product according to the present invention it is desirable that the components therein are chosen so that its osmotic pressure is as low as possible without affecting the composition of the beverage product in a disadvantageous manner.

An essential blood sugar level-increasing components in the beverage product according to the invention a mixture of oligosaccharides is used, having DP values in the range 2–10, especially 3–10, which have a low or no sweetening effect and a bland taste. It is preferred that the oligosaccharides have such a composition that their average DP value is within the range 3–5. So as to make the beverage product well-tasting it may contain aroma components and/or taste-improving substances. Such aroma components are commonly known and can be chosen as desired. As taste-improving substances syntetical sweetening agents can be used such as sodium saccharinate or sodium cyclamate. However, sweetening sugars can also be used, preferably disaccharides such as saccharose. Addition of monosaccharides should be avoided since they cause a greater increase of the osmotic pressure in relation to the carbohydrate content. Sweetening sugars such as saccharose can be present in an amount up to 7% of the beverage product.

The use of the above-defined oligosaccharide mixture enables formulation of a beverage product with a very high carbohydrate content which is desirable for a beverage product primarily intended for a rapid increase of the glucose-content of the blood. The oligosaccharide content can in such cases be made as high as 25% of the beverage product even if such high contents are not commonly used. On the other hand, when it is desired to formulate a beverage product primarily intended for administration of water the content of oligosaccharides can be kept low, usually down to 3% of the weight of the beverage product.

The content of oligosaccharides with a DP in the range 2–10 of the beverage product is thus kept within the range of 3–25%, based on the weight of the beverage product.

It may be suitable and in certain cases preferred that the beverage product contains mineral salts of the kind occurring in body liquids, e.g. sodium chloride, potassium chloride and also phosphates of the said metals. During heavy muscle work, especially at high ambient temperatures, the body strives to decrease an increased body temperature by perspiration. The perspired liquid contains such mineral salts. During relatively short periods of work it is, however, not necessary from a physiological point of view to replace salts lost by perspiration. This is only necessary after very long periods of perspiration. Accordingly, the mineral salt content of the beverage product is not at all critical and may be from 0 up to a few percent, e.g. up to 3% of the beverage product.

Further to the oligosaccharide mixture with a DP value in the range 2–10 as defined above the beverage product shall contain one or more physiologically acceptable alkalising compounds or a combination of such compounds in such an amount that they after consumption of the beverage product in a regular manner during heavy continuing muscle work cause an increase of the pH of the ventricular contents from the normal value which certainly varies from one individual to another but usually is about 1–2. This pH increase of the ventricular contents shall according to the invention be such that the pH value is increased to a value above 3.5, preferably above 4.5. It may be desired to achieve a pH value in the ventricular contents which is above 7.0, i.e.

an alkaline pH value. This pH increase will cause an almost immediate opening of the pylorus so that the ventricular contents very rapidly passes into the duodenum where the oligosaccharides rapidly are depolymerised to glucose which together with water is directly absorbed into the blood.

As physiologically acceptable alkalizing compounds several different salts, oxides or buffering substances may be used. Non-limiting examples of such compounds or substances are sodium bicarbonate, potassium bicarbonate, magnesium bicarbonate, magnesia, aluminium hydroxide. Non-watersoluble alkalizing agents can be used suspended in the beverage product. The water-soluble alkali metal bicarbonates are preferred alkalizing compounds or pH buffering compound combinations.

The contents of for instance sodium bicarbonate which gives the desired pH increase in the ventricular contents is usually 0.5–10 grams/liter of the beverage product, preferably 3–5 grams/liter. However, the content of the physiologically acceptable alkalising compound or compound combination can be much higher, viz. up to 20 grams/liter or more. Such high contents can be of value also for other purposes than the pH increase of the ventricular contents. According to the invention it has thus been found that a great alkalizing capacity in the beverage product can exert a neutralising effect on lactic acid formed in the tissues during heavy muscle work so that the recovery period will be considerably shortened.

From the above follows that the invention relates to a beverage product, especially adapted for rapid administration of water and carbohydrates during periods of heavy muscle work, which is characterized by consisting of a preferably monosaccharide-free solution, which contains 3–25% by weight of soluble oligosaccharides with a DP value in the range 2–10, the average DP value of the oligosaccharide mixture preferably being 3–5; at least one physiologically acceptable alkalizing compound or compound combination; and optionally salts of the type occurring in body liquids and suitably components improving the aroma and taste of the beverage product, all in minor amounts; the content of the physiologically acceptable compound or compound combination in the beverage product being such that it after consumption of the beverage product during heavy muscle work, e.g. at 60% of the maximal aerobic capacity, in an amount of 250 ml each fifteenth minute during one hour gives an increase of the pH in the ventricular contents to at least 3.5, preferably at least 4.5 and most preferred 7.0 or higher.

The beverage product according to the invention is thus a solution which may contain suspended substances. However, the invention also comprises the beverage product in the dry solid form which can be reconstituted to the finished beverage product by addition of water.

The invention also comprises a process for preparing the defined beverage product, which process is characterized in that essentially completely water-soluble oligosaccharides with DP values in the range 2–10, the average DP values of the same being 3–5, together with a physiologically acceptable alkalizing compound or compound combination and optionally mineral salts and aroma and taste-improving substances, the latter in minor amounts, are dissolved and/or dispersed in water in such an amount that the finished solution contains 3–25% by weight of the above-defined essentially soluble oligosaccharides with a DP value in the range 2–10; and the physiologically acceptable compound or compound combination in an amount from 0.5 grams/liter to 20 grams/liter, especially above 3 grams/liter.

Finally, the invention also comprises a process for rapidly replacing water lost by perspiration and for preventing a decrease of the glucose content of blood during periods of heavy muscle work, characterized by per os administrating a beverage product with the above-defined composition.

Practical experiments have been performed in which beverage products according to the invention have been compared with a product according to the closest prior art, i.e. the U.S. Pat. No. 4,312,856. In the experiments three beverage products (test solutions) were used, the compositions of which are defined below:

| | | |
|---|---|---|
| I Product according to Example 2 in US-A-4 312 856 (osmotic pressure = 4.82 atm at 25° C.) | | |
| II Oligosaccharides DP 2-10 | 75 | g |
| Potassium chloride | 0.15 | g |
| Sodium bicarbonate | 1.03 | g |
| Aroma | 1.00 | g |
| Water ad | 1000 | g |
| (osmotic pressure = 4.66 atm at 25° C.) | | |
| III Oligosaccharides DP 2-10 | 75 | g |
| Potassium chloride | 0.15 | g |
| Sodium bicarbonate | 5.15 | g |
| Aroma | 1.0 | g |
| Water ad | 1000 | g |
| (osmotic pressure = 5.79 atm at 25° C.) | | |

The test solutions II and III are according to the present invention.

The experiments were performed with the use of seven healthy volunteers with experience of bicycle competition (men, ages 18–50 years) and with use of ergometer bicycles (Monark ®). During the tests pulse frequencies, blood sugar levels, the emptying rate of the ventricle and the pH of the ventricular contents were determined.

The maximum oxygen uptake of the test participants were determined separately, the work being performed with stepwise increasing loads on bicycle ergometers and the expirated air was recovered in Douglas sacks. The contents of oxygen and carbon dioxide of the air were analysed in a Centronik ® analysator. The maximum oxygen uptake for the test participants was in average 4.1 liters/minute (range 3.7–4.6 liters/minute).

The test participants performed work on the ergometer bicycles during 1.5 hours for each of the three test solutions at 60% of their respective maximum aerobic capacity.

Figure 1:
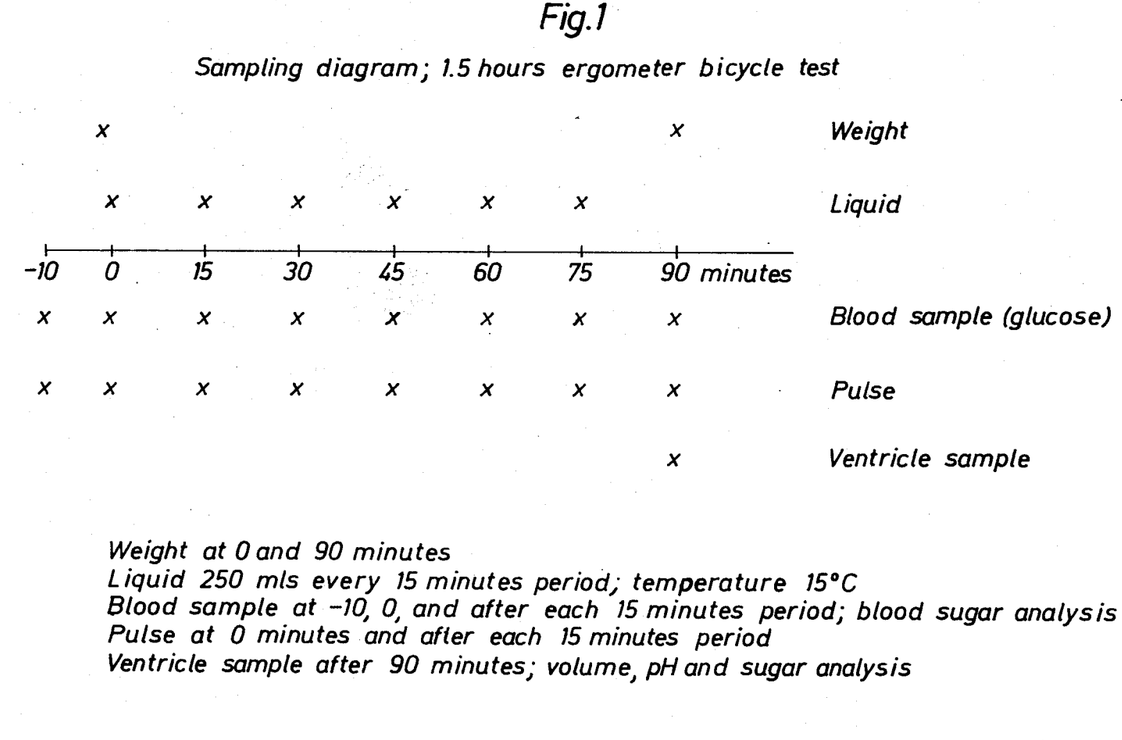

During the work period blood samples were taken from the elbow vein each fifteenth minute for analysis of the glucose content partly at rest and partly during work; the pulse frequency was determined simultaneously. The test participants consumed 1000 mls/hour of the test solutions which were temperated to ±15° C., divided in four portions of 250 mls each fifteenth minute immediately after each blood sampling. FIG. 1 shows how the sampling was performed.

After the total work period of 1.5 hours the remaining each of the ventricle contents was coloured with 10 mls of phenol red (0.4 mg/ml) and a duodenal sond no. 12 was introduced through the nose down to the ventricle and about 20 mls of the ventricular contents was sucked up with a 50 mls syringe. The ventricular samples were analysed as regards pH, suger content and the volume of the remaining test solution was determined by measurement of the colour intensity in a spectrophotometer at 520, 560 and 600 nm (according to Schedl, 1966) after addition of a borax buffer.

Figure 2:
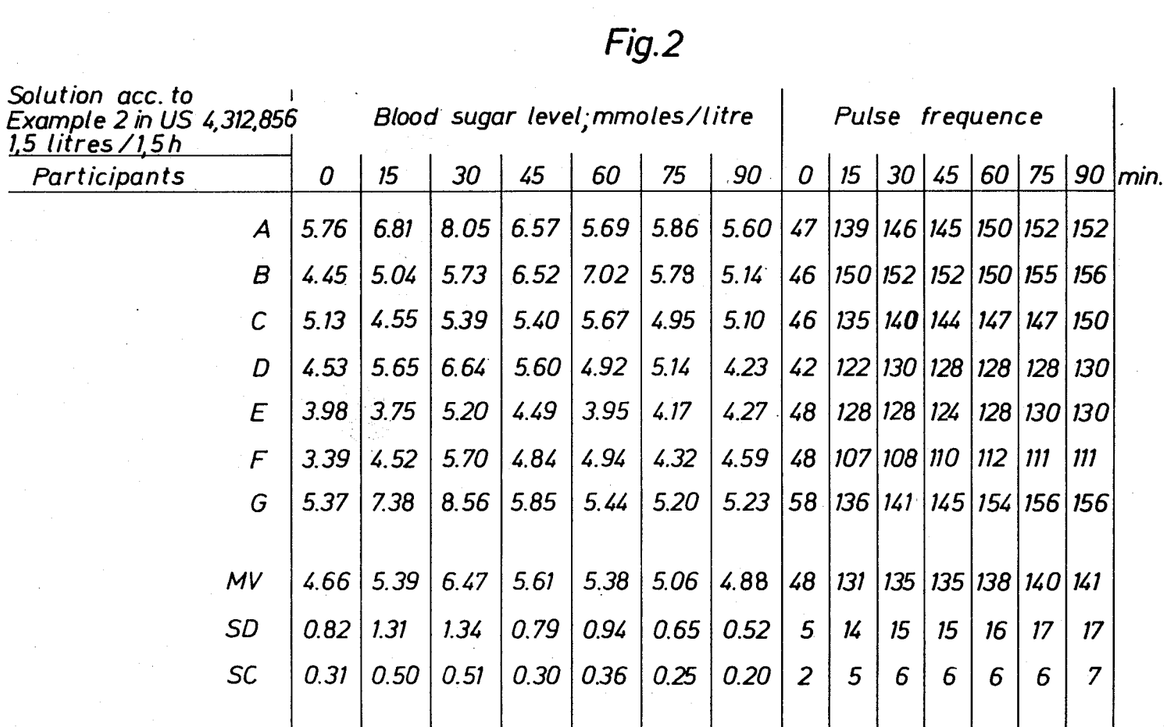
Figure 3:
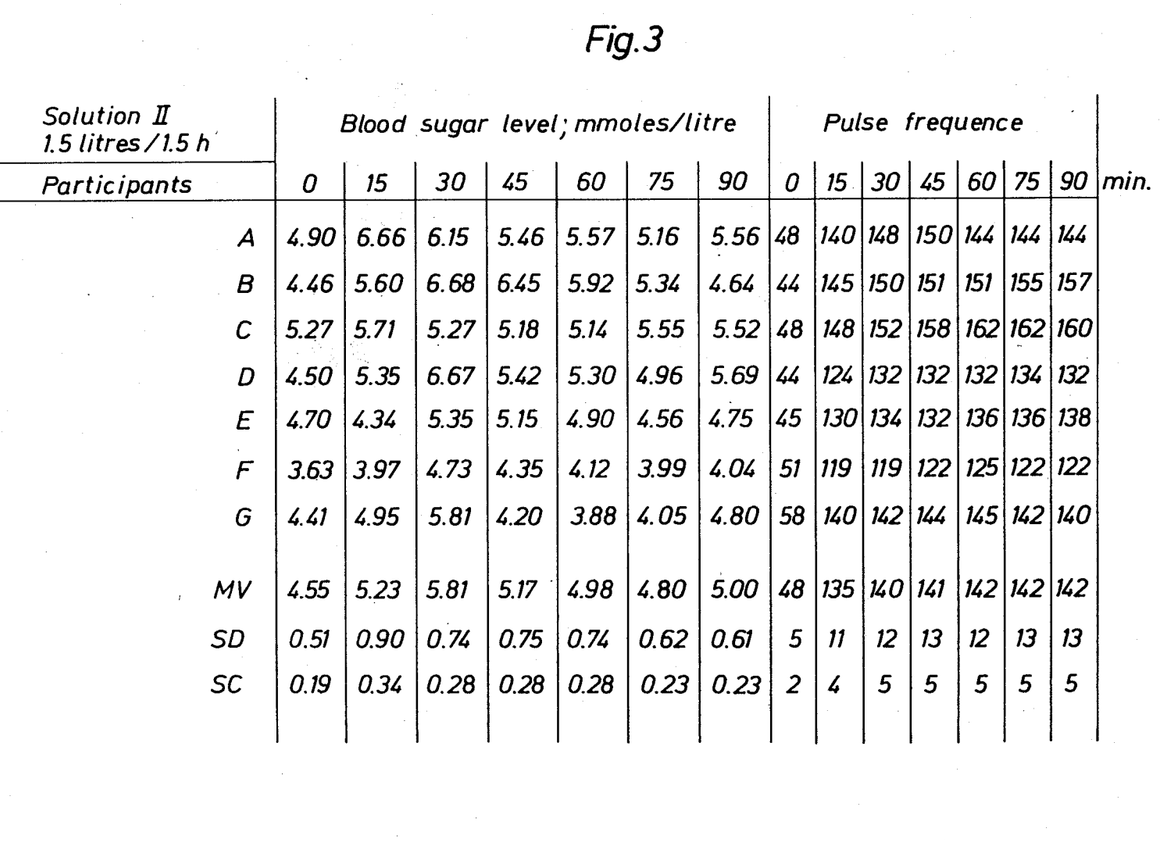
Figure 4:
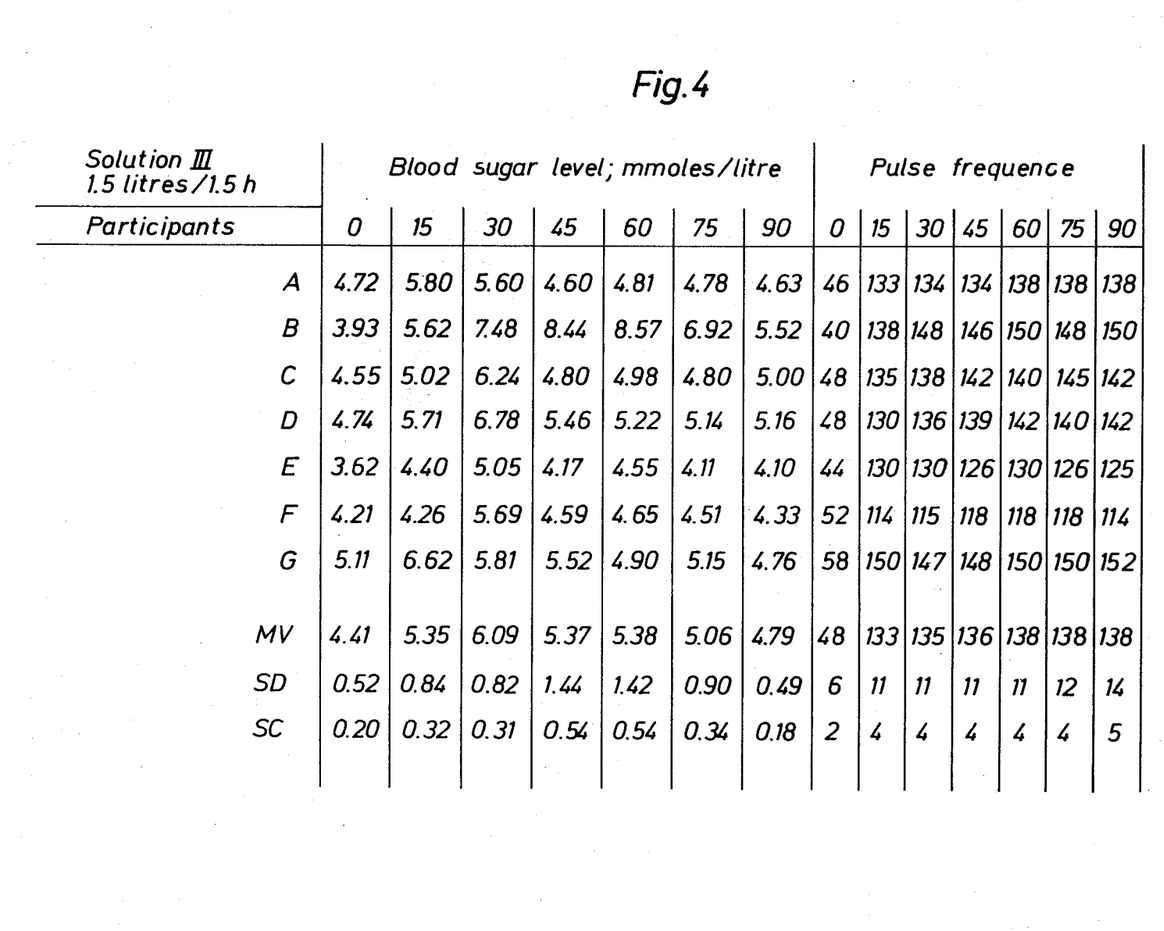
Figure 5:
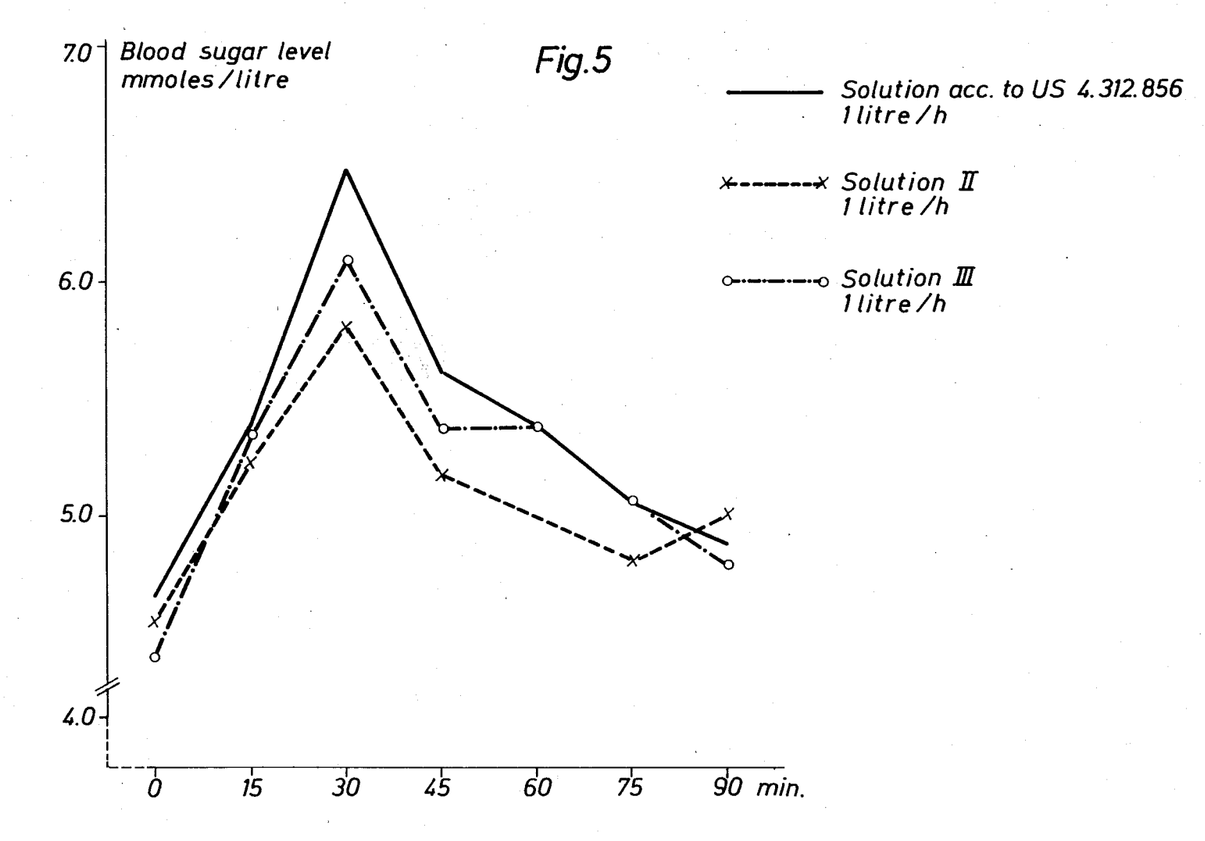

In FIGS. 2–4 the blood sugar contents and the pulse frequency values are summarized. The average values of the blood sugar contents were found to change in a manner which corresponds with the one elucidated in FIG. 3 in the U.S. Pat. No. 4,312,856, viz. with a maximum for all test solutions after 30 minutes, which is elucidated in FIG. 5. The differences between the test solutions is within the range of variation which also is true for the pulse frequency.

Figure 6:
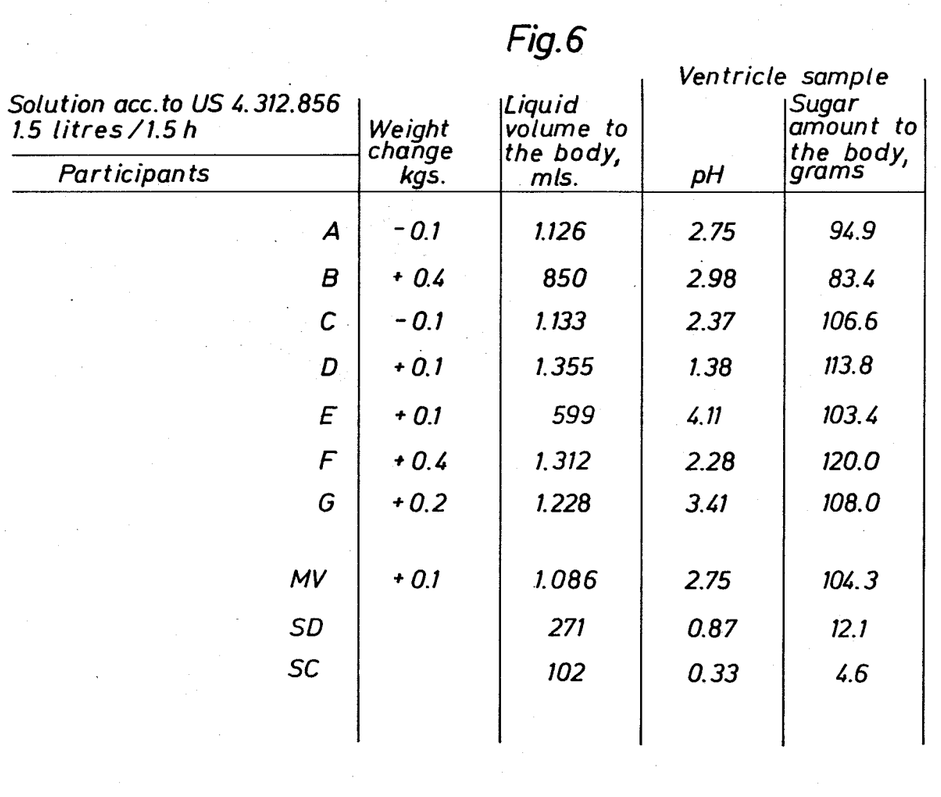
Figure 7:
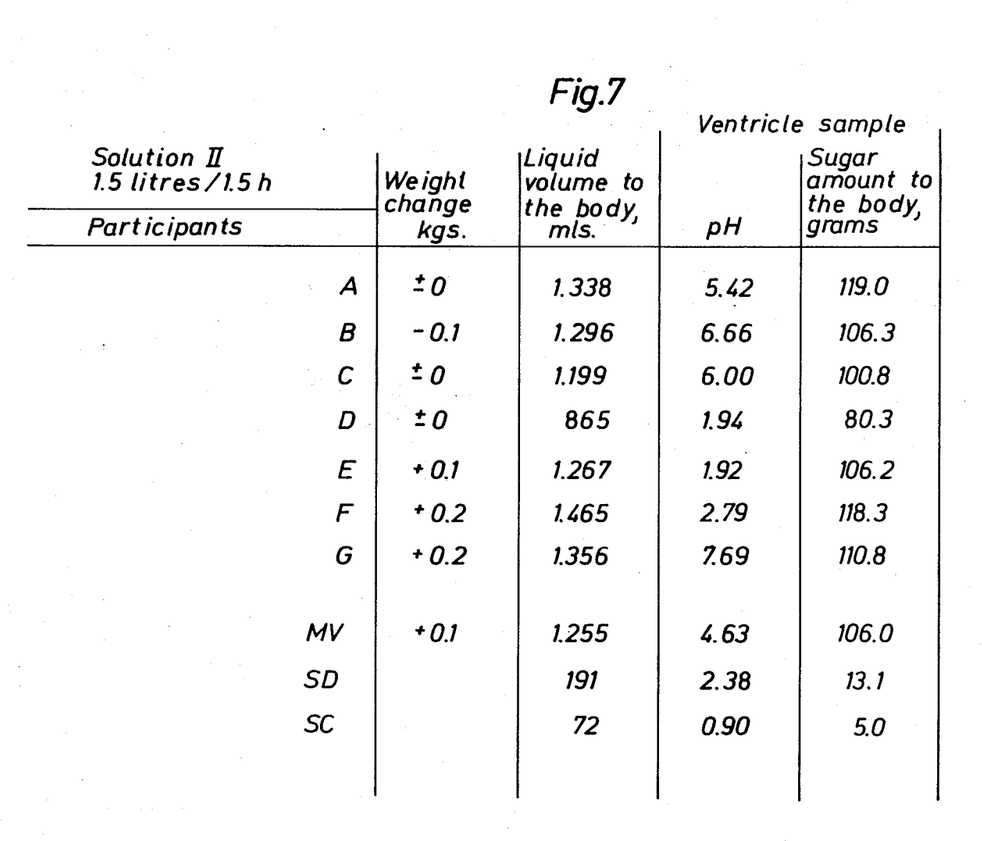
Figure 8:
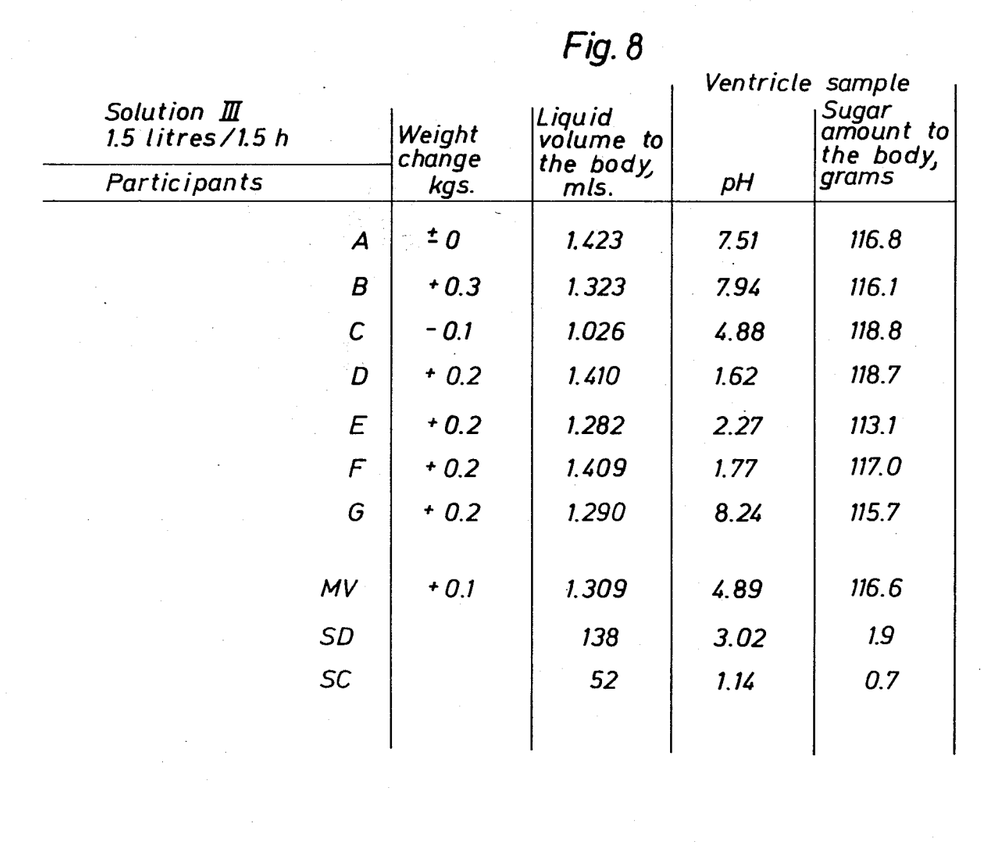

FIGS. 6–8 summarizes the results from analysis of samples taken from the ventricle and the change of body weight. The average value of the determined pH values did increase from 2.8 to 4.6 and 4.9. Three test participants still had an acid pH in the ventricle after the administration of 5.15 grams/liter bicarbonate which is due to the fact that the liquid volume in the ventricle was so small that the acid ventricle secrete dominates. The emptying rate of the ventricle increased by administration of bicarbonate for all three test participants. The average value of the liquid volume passing the pylorus did by the addition of bicarbonate in an amount of 1.03 grams/liter increase with 16% and in an amount of 5.15 grams/liter with 20% and the carbohydrate passage from the ventricle increased with 2 and 12% resp.

The above experimental results show that the invention provides increased possibilities to effectively replace losses of liquid during heavy muscle work and to simultaneously supply the body with energy in the form of carbohydrates.

The invention is elucidated by the following non-limiting examples.

EXAMPLE 1

This example gives the composition of a beverage product adapted for introducing considerable amounts of liquid and energy (the normal case):

|  | grams/liter beverage |
|---|---|
| oligosaccharides DP 2-10 (average molecular weight 530) | 75 |
| $NaHCO_3$ | 2.5 |
| $KHCO_3$ | 2.5 |
| Aroma | q.s. |
| (osmotic pressure at 25° C. = 3.42 atm.) | |

EXAMPLE 2

This example gives the composition of a beverage product adapted for restoring the muscle strength after muscle work:

|  | grams/liter beverage |
|---|---|
| oligosaccharides DP 2-10 (average molecular weight 530) | 75 |
| $NaHCO_3$ | 10 |
| $KHCO_3$ | 10 |
| Aroma | q.s. |
| (osmotic pressure at 25° C. = 56.37 atm.) | |

EXAMPLE 3

This example gives the composition of a beverage product adapted for introducing large amounts of energy in connection with heavy muscle work:

|  | grams/liter beverage |
|---|---|
| oligosaccharides DP 2-10 (average molecular weight 1158) | 230 |
| $NaHCO_3$ | 2.5 |
| $KHCO_3$ | 2.5 |
| Aroma | q.s. |
| (osmotic pressure at 25° C. = 7.15 atm.) | |

We claim:

1. Beverage product, especially adapted for rapid oral administration of water and carbohydrates to the human body during periods of heavy muscle work, characterized in that it consists of a solution, which contains 3–25% by weight of a mixture of soluble oligosaccharides with DP values between 2 and 10 inclusive, at least one physiologically acceptable alkalizing compound in an amount of 0.5–20 grams/liter of beverage the solution's content of the physiologically acceptable alkalizing compound being such that when the beverage is consumed during heavy muscle work that is at about 60% of the maximal aerobic capacity in an amount of 250 mls each fifteen minutes during one hour gives an increase of the pH value in the stomach ventricle contents to 3.5 to about 8.5.

2. Beverage product according to claim 1, characterized in that the physiologically acceptable alkalizing compound contains sodium bicarbonate, potassium bicarbonate, magnesium bicarbonate, magnesia, aluminium hydroxide, or mixtures thereof.

3. Beverage product according to claim 2, characterized in that the solution exerts its buffering effect within the pH range 4–8.5.

4. Beverage product according to claim 1, 2 or 3, characterized in that it is in the essentially dry solid form for reconstitution by the addition of water.

5. A beverage product according to claim 2 wherein the content of the alkalizing compound is in the range of 3–20 grams/liter.

6. A beverage product according to claim 1 wherein the average DP value of the oligosaccharide is in the range of 3–5.

7. A beverage product according to claim 1 wherein the pH is increased to above 4.5.

8. A beverage product according to claim 1 wherein the pH is increased to above 7.0.

9. A beverage product according to claim 1 which is essentially monosaccharide-free.

10. A beverage product according to claim 1 which additionally contains salts occurring in body liquids and suitable aroma and taste-improving substances, in minor amounts.

11. A process for rapidly replacing water lost by perspiration and preventing a decrease of the glucose content of blood or for increasing the same during periods of heavy muscle work by humans, characterized by per os administrating a beverage product to said humans as defined in claim 1, 2 or 3.

* * * * *